United States Patent [19]

Rubino et al.

[11] 4,137,306

[45] Jan. 30, 1979

[54] ANHYDROUS ANTIPERSPIRANT STICK COMPOSITIONS

[75] Inventors: Andrew M. Rubino, New Providence; John J. Margres, Old Bridge, both of N.J.

[73] Assignee: Armour Pharmaceutical Company, Phoenix, Ariz.

[21] Appl. No.: 367,310

[22] Filed: Jun. 5, 1973

[51] Int. Cl.² .................. A61K 7/34; A61K 7/36; A61K 7/38
[52] U.S. Cl. ................................. 424/68; 424/66; 424/67; 424/DIG. 5
[58] Field of Search .................. 424/68, 14, 66, 67, 424/DIG. 5

[56] References Cited

U.S. PATENT DOCUMENTS

| | | | |
|---|---|---|---|
| 2,890,987 | 6/1959 | Hilfer | 424/68 X |
| 2,970,083 | 1/1961 | Bell | 424/68 |
| 3,255,082 | 6/1966 | Barton | 424/14 |
| 3,259,545 | 7/1966 | Teller | 424/68 |
| 3,325,367 | 6/1967 | Miechowski | 424/67 |
| 3,472,929 | 10/1969 | Jones et al. | 424/68 X |
| 3,507,896 | 4/1970 | Jones et al. | 424/68 X |
| 3,523,130 | 8/1970 | Jones et al. | 424/68 X |
| 3,555,146 | 1/1971 | Jones et al. | 424/68 X |

FOREIGN PATENT DOCUMENTS

| | | | |
|---|---|---|---|
| 1122221 | 1/1962 | Fed. Rep. of Germany | 424/68 |
| 1192021 | 5/1970 | United Kingdom | 424/68 |

*Primary Examiner*—Frederick E. Waddell
*Attorney, Agent, or Firm*—Richard R. Mybeck; William W. Schwarze

[57] ABSTRACT

Improved antiperspirant stick compositions are provided which comprise a substantially anhydrous, homogeneous mixture of an alcohol soluble astringent basic aluminum compound as the active ingredient in a solid or semi-solid system including an alkylene polyhydric alcohol, a normally solid higher fatty acid amide of an alkylolamine in which the fatty acid radical contains at least 12 carbon atoms and the alkylol groups of the alkylolamine contain from 2 to 3 carbon atoms, and a non-toxic dermatologically acceptable non-aqueous solvent, such as ethanol, for the astringent basic aluminum compound. The mixture provides a highly esthestic, stable and quite effective antiperspirant in stick form suitable for application to the human axilla.

15 Claims, No Drawings

ANHYDROUS ANTIPERSPIRANT STICK COMPOSITIONS

BACKGROUND OF THE INVENTION

The present invention relates to anhydrous antiperspirant stick compositions. More particularly, the invention is directed to esthetic and efficacious antiperspirant compositions based on anhydrous basic aluminum systems in stick form for application to the human axilla.

It has been known in the art for many years to prepare various cosmetic compositions, including deodorants and antiperspirants, in stick form, such as the well-known cologne sticks or soap sticks. Such cologne sticks or soap sticks were very popular due to their high degree of cosmetic elegance. Unfortunately, these hard, gel-like formulations were unsuitable for use in making stick form antiperspirant compositions.

Thus, the cologne stick or soap stick formulations were based upon sodium stearate-ethanol-water emulsions. Such soap base emulsions are incompatible with the usual active antiperspirant ingredients, particularly the acidic, astringent aluminum salts. As a consequence, attempts have been made for many years to achieve the elegance of the cologne stick via other avenues in order to accommodate the aluminum salts. However, such attempts have never been completely successful for a number of reasons, including decreased efficacy of the aluminum salts and failure to duplicate the high degree of cosmetic elegance of the cologne sticks.

One such early attempt at solving these problems is U.S. Pat. No. 2,890,987 issued to Hilfer on June 16, 1959 and assigned to Witco Chemical Company. According to this patent, the sodium stearate or soap base system was replaced by the combination of a solid fatty acid amide of an alkylolamine and an alkylene polyhydric alcohol. While such systems were apparently compatible with the active aluminum salts, they lacked a high degree of cosmetic elegance. Thus, such stick formulations had a very wet feel and slow drying characteristics due to the presence of about 10 to 25 weight percent of water in the formulations.

Other notable attempts at solving these problems are represented in U.S. Pat. Nos. 2,732,327; 2,933,433; 2,970,083; 3,255,082; 3,259,545 and 3,553,316. These patents illustrate attempts to solve the problems by means of either providing a stabilizing ingredient for the sodium stearate or soap base or complexing of the aluminum salt in order to render it compatible with various soap bases. However, in many of these cases the achievement of compatibility was compromised by reductions in the efficacy of the aluminum antiperspirant compounds. Moreover, in each of these cases, superior cosmetic elegance was not achieved due primarily to a wet feel and slow drying characteristics from the high percentages of water present in the formulations.

More recently, at least one proprietary antiperspirant formulation has been developed based upon the system disclosed in the Hilfer U.S. Pat. No. 2,890,987. Such formulation includes about 30 weight percent Emcol 70 (a stearic acid monoethanolamide), about 28 percent propylene glycol, about 15 percent Emcol 249-3K (a propoxylated alcohol emollient), about 20 weight percent Rehydrol (a propylene glycol complex of basic aluminum chloride according to U.S. Pat. No. 3,420,932) and about 7 percent water. Although such composition produces a quite satisfactory antiperspirant stick in many respects, it is still rather slow drying, hard and lacking in good slip-feel and other esthetic characteristics.

BRIEF SUMMARY OF THE INVENTION

The above and other deficiencies and problems of the prior art are alleviated and solved by the astringent or antiperspirant stick compositions of the present invention which comprise a table, substantially anhydrous, homogeneous mixture of about 5 to 20 weight percent of an alcohol soluble astringent basic aluminum compound, about 20 to 35 weight percent of an alkylene polyhydric alcohol, about 20 to 30 weight percent of a normally solid higher fatty acid amide of an alkylol amine in which the fatty acid radical contains at least 12 carbon atoms and the alkylol groups of said alkylol amine contain from 2 to 3 carbon atoms, and about 1 to 40 weight percent of a non-toxic dermatologically acceptable nonaqueous solvent for the astringent basic aluminum compound. Such compositions produce a highly esthetic antiperspirant in stick form suitable for application to the human axilla. In particular, the compositions have excellent drying characteristics, superior slip-feel, superior antiperspirant efficacy and good shelf life and stability, particularly as tested by a freeze-thaw cycle.

DETAILED DESCRIPTION OF PREFERRED EMBODIMENTS

The active ingredients used in the system of the present invention may be generally classified as alcohol soluble basic aluminum compounds or other metallic derivatives or complexes thereof which have sufficient astringency to be effective as perspiration inhibitors. A number of these basic aluminum compounds or complexes which are soluble in alcohol or other non-aqueous solvents have been developed in the last ten years or so and are well known to the art. Many of these are suitable for use in the system of the present invention. Examples of suitable alcohol astringent basic aluminum compounds for use in the present invention are the following:

(1) Polyhydroxy complexes of basic aluminum salts. These complexes or coordination compounds are described in detail in U.S. Pat. No. 3,420,932 to Jones et al., entitled "Methods of Making Alcohol Soluble Complexes of Aluminum and Preparations Employing the Complexes". This category of complexes may be represented by the general formula:

$$Al_2(H_2O)_{y-z}(OH)_{6-nx}(A)_n(R)_z$$

wherein A is selected from the class consisting of chloride, bromide, iodide, sulfate and sulfamate; R is the coordinating moiety of a polyhydroxy compound having a carbon chain in which at least two carbon atoms link a hydroxyl group to said chain, n is a positive integer of from 1 to 4; x is the valence of A, y is a value of about 0.5 to 6 and is always such that (y-z) does not give a negative value; and z is the number of available coordination sites, with nx being from 1 to 4.

Suitable polyhydroxy compounds for use in the above formula include: propylene glycol; 1,1,1-trimethylol propane, 1,3-butylene glycol (1,3-butane-diol); glycerine (1,2,3-trihydroxy propane); 2-methyl-2,4-pentane-diol; neopentyl glycol (2,2-dimethyl-1,3-dihydroxy pentane); polyethylene glycol (mol. wt. = 400); Polyglycol 15-200 (a Dow material having an ethereal linkage between propylene oxide and ethylene and condensed with glycerine in which each chain has a terminal hydroxy group (mol. wt. = 2700); p-xylene α,α diol; and polyepichlorohydrin; butyne-1,4 diol; 2-ethyl-1,3-hexane-diol; and polypropylene glycol (av. mol. wt. = 400).

The above polyhydroxy complexes may be made according to the methods described in U.S. Pat. No. 3,420,932, the disclosure of which is incorporated herein by reference.

Particularly preferred polyhydroxy complexes of the above formula for use in the present invention are those prepared from basic aluminum chlorides and propylene glycol and having the general formula:

$$Al_2(H_2O)_{0.7-1.1}(OH)_{4.9-5.1}(Cl)_{0.9-1.1} \text{ (1,2 propylene glycol)}_{0.7-1.3}$$

In the above formula, the 1,2 propylene glycol may be present in the complex in a number of ways, namely with both carbinol hydrogen atoms being lost by condensation or neutralization, or with only one carbinol hydrogen atom being lost by condensation or neutralization, or with both hydroxy groups remaining intact and coordinated and/or chelated to one of the aluminum atoms. The above preferred complexes are commercially available from Reheis Chemical Company, a division of Armour Pharmaceutical Company, under the trademark "Rehydrol".

(2) Basic aluminum bromides. It has recently been found that certain basic aluminum bromides are highly soluble in alcohol and other non-aqueous solvents and are highly effective as antiperspirants. These basic aluminum bromides which, are suitable for use in the present invention, are described in detail in U.S. patent application Ser. No. 88,206, filed Nov. 9, 1970 by Jones et al. for "Basic Aluminum Bromide Compositions", and may be represented by the general formula:

$$Al_2(OH)_x Br_y \cdot XH_2O$$

wherein x may be from about 4.8 to 5.1 and y may be from about 0.9 to 1.2 such that x+y = 6, and X may vary from about 2.0 to 3.4. These 5/6th basic aluminum bromide compounds may be prepared according to the methods described in application Ser. No. 88,206, which is hereby incorporated herein by reference.

(3) Basic aluminum chlorides. It has also recently been found that certain basic aluminum chlorides may be rendered alcohol soluble by heating an aqueous solution of the basic aluminum chlorides under reflux conditions and then drying the solution under carefully controlled conditions to a critical percentage of free and coordinated water. Such alcohol soluble basic aluminum chlorides are described in detail in U.S. patent application Ser. No. 84,093, filed Oct. 26, 1970 by Jones et al. for "Alcohol Soluble Base Aluminum Chlorides and Method of Making Same". These basic aluminum chlorides are suitable for use in the present invention, and the disclosure of application Ser. No. 84,093 is incorporated herein by reference. Particularly preferred for use in the present invention are the alcohol soluble basic aluminum chlorides having an Al/Cl mol ratio of about 1.9 and a calculated weight percent of free and coordinated water of about 18 to 20.

(4) Polyhydroxy derivatives of zinc and zirconium complexes of basic aluminum halides. These polyhydroxy derivatives which are suitable for use in the present invention are fully described in U.S. Pat. No. 3,405,153 to Jones et al. for "Metal-Aluminum Inorganic-Organic Complexes and Methods of Preparing the Same", the disclosure of which is incorporated herein by reference. These alcohol soluble complexes may be defined by the general formula:

$$nQ \cdot Al_2(OH)_{4.5} A_{1-2} R_{1-4} (H_2O)_{0.5-4}$$

wherein Q is a member of the ground consisting of zinc chloride, zinc iodide, zinc bromide, zinc hydroxy chloride, zinc hydroxy iodide, zinc hydroxy bromide, zirconyl chloride, and zirconyl hydroxy chloride; A is an anion selected from the group consisting of chloride, bromide and iodide; R is the coordinating moiety of a polyhydroxy compound having at least two carbon atoms to which are attached at least two hydroxy groups, and n is the number of moles of Q and is at least 0.05. The polyhydroxy compounds (R) used in the above formula may be selected from the same list as that given above for the polyhydroxy complexes of basic aluminum salts.

(5) Zinc and zirconium derivatives of basic aluminum bromides. Alcohol soluble zinc and zirconium derivatives of basic aluminum bromides which may be used in the method of the present invention are described in detail in U.S. patent application Ser. No. 164,433 of Jones et al., filed July 20, 1971 for "Zinc and Zirconium Complexes of Basic Aluminum Bromides and Methods of Making Same", the disclosure of which is incorporated herein by reference. These alcohol soluble complexes may be represented by the empirical formula:

$$[Al_2 (OH)_{6-x} Br_x]_{(y/2)} \cdot A$$

in which x = about 0.9 to 1.2, y = about 3 to 20, A is a compound selected from the group consisting of zinc chloride, zinc bromide, zirconyl chloride, zirconyl bromide, zirconyl hydroxychloride, zirconyl hydroxybromide, and mixtures thereof. These complexes may be made by the methods described in application Serial No. 164,433.

(6) Phenol sulfonate complexes of basic aluminum chlorides. Alcohol soluble phenol sulfonate complexes of basic aluminum chlorides which may be used in the method of the present invention are described in U.S. Pat. No. 3,634,480 to Sheffield, entitled "Complexes Containing Aluminum Chlorhydroxide". These complexes may be represented by the formula:

$$[Al_2(OH)_5Cl \cdot (H_2O)_y][M(C_6H_4OHSO_3)_x]$$

wherein M is H or an aluminum or zinc ion and x is an integer equal to the valence of M, and y is an integer from 2 to 4, and wherein the molar ratio of the aluminum chlorhydroxide moiety to the phensolsulfonate moiety of said complex is in the range from about 1 to 12:1. The complexes of the above formula may be made according to the methods described in U.S. Pat. No. 3,634,480, the disclosure of which is incorporated herein by reference.

It will be understood that the above are only representative of the various alcohol soluble astringent basic aluminum compounds which are most suitable for use in the present invention. Thus, other alcohol soluble astringent basic aluminum compounds may also be used, as well as combinations and mixtures of the above basic aluminum compounds either with each other or with other basic aluminum compounds, buffers, etc. Examples of other alcohol soluble astringent basic aluminum compounds suitable for use in the stick compositions of the present invention might include the alcoholated basic aluminum halides described in U.S. Pat. No. 3,692,811 to Gilman et al., the zinc and zirconium complexes of basic aluminum chlorides described in U.S. patent application Ser. No. 164,434 of Jones et al., alcohol soluble basic aluminum sulfamates, alcohol soluble basic aluminum iodides, and others. Additionally, mixtures of basic aluminum compounds with other astringent salts may be used, such as the buffered mixtures with zirconyl chloride octahydrate in U.S. Pat. No. 2,814,584 to Daley.

Particularly good antiperspirant efficacy may be achieved by adding to the alcohol soluble basic aluminum compound an amount of aluminum chloride hexahydrate ($AlCl_3.6H_2O$) up to about 25 percent based on the weight of the alcohol soluble basic aluminum compound or up to about 4 weight percent based on the weight of the total stick composition. It is generally believed in the art that the aluminum chloride hexahydrate produces a synergistic effect in the antiperspirant efficacy of the overall formulation, and this additive may be advantageously used in the present invention.

Since the addition of aluminum chloride hexahydrate yields a very acid pH in the solution, it is necessary to also add a buffer in order to produce a dermatologically acceptable antiperspirant. That is, the composition must be buffered up to at least a pH of 3 in order that the antiperspirant stick not be too acid. In order not to destroy or adversely affect the antiperspirancy of the overall stick, it is preferred that an organic buffer solution be used. Moreover, in order to maintain a substantially anhydrous stick composition, a buffer which is soluble in a non-aqueous solvent must be selected. One particularly suitable buffering agent which meets these criteria is urea, which may suitably be added in a solution of propylene glycol. Other suitable buffering agents will be apparent to those of ordinary skill in the art. The relatively high concentration (compared to antiperspirant spray solutions) of $AlCl_3.6H_2O$ which may be added to formulations of the present invention is apparently due to the unexpected buffering action of the stick formulation, particularly the alkylolamides. Moreover, the physical characteristics of the stick do not require the prolonged solution stability of the spray solutions.

The alcohol soluble astringent basic aluminum compound should be present in the stick composition in an amount of about 5 to 20 weight percent, and preferably about 15 to 20 weight percent. While percentages greater than 20 weight percent could of course be used, no significant increase in antiperspirant efficacy would be achieved and this would be more costly and wasteful. Similarly, amounts below about 5 weight percent have little antiperspirant efficacy and would fall in the range of deodorant rather than antiperspirant compositions, the deodorant characteristics being due to the antimicrobial effects of the aluminum compounds.

Suitable alkylene polyhydric alcohols for use in the antiperspirant stick compositions of the present invention include propylene glycol, ethylene glycol, diethylene glycol, butylene glycol, and various other glycols such as the higher polyethylene glycols and polypropylene glycols. In general, propylene glycol is particularly satisfactory, and the greater the molecular weight or chain length of the polyglycols, the less satisfactory such polyhydric alcohols become. The alkylene polyhydric alcohols can be either solid or liquid at room temperature, but it is preferred that they be liquid.

The alkylene polyhydric alcohols should be present in an amount of about 20-35 weight percent of the total composition. Since polyhydric alcohols such as propylene glycol also have certain solvent and humectant properties, the amount of such compounds used in the antiperspirant stick composition may be adjusted according to the amounts of other solvents and humectants in the overall composition, and depending upon the particular astringent aluminum compound employed in the composition.

The normally solid higher fatty acid amides of alkylolamines useful in the antiperspirant stick compositions of the present invention are generally the same as those mentioned in U.S. Pat. No. 2,890,987 to Hilfer. Such amides can be derived by the usual condensation, at somewhat elevated temperatures, for instance, 150 to 175 degrees C., of normally solid higher fatty acids (or other higher fatty acid acylating compounds) such as palmitic acid, stearic acid, myristic acid, lauric acid, and the like, with primary or secondary alkylolamines or hydroxyalkyl amines, namely those which contain one or more hydroxy groups and, in addition, at least one primary or secondary amino group. Illustrative examples of such alkylolamines or hydroxyalkyl amines are, for instance, monoethanolamine, diethanolamine, n-propanolamine, monoisopropanolamine, diisopropanolamine, hydroxyethyl ethylenediamine, glycerolamine; 1-amino-2,3-propanediol; and 2-amino-1,3-propanediol. It will be noted that the alkylol groups present in said alkylolamines or hydroxyalkyl amines contain from 2 to 3 carbon atoms.

Preferred higher fatty acid amides of alkylolamines for use in the present invention include the condensation products of myristic acid, palmitic acid or stearic acid with monoethanolamine. Particularly suitable is stearic acid monoethanolamide, one form of which is commercially available under the trademark Emcol 70 of Witco Chemical Company. It is of course understood that mixtures of the higher molecular weight normally solid fatty acids (at least 12 carbon atoms) and commercial mixtures of the alkylolamines can be utilized. The alkylolamides, which are also normally solid, should be present in the compositions of the present invention to an extent of about 20 to 30 weight percent of the total composition, and preferably about 25-28 percent.

A crucial feature in achieving the esthetic properties of the compositions of the present invention is the replacement of the substantial amounts of water (characteristic of previous stick formulations) with a non-aqueous, non-toxic, dermatologically acceptable organic compound which is a solvent for the astringent aluminum compound. In addition to being non-aqueous, non-toxic for human use and dermatologically acceptable (i.e., neither too acidic or too basic), such solvents should preferably have relatively low boiling points in order to achieve optimum drying characteristics. Particularly preferred solvents for use in the present invention are ethanol (which is available in many approved denatured forms such as SDA-40, SDA-39C, etc.), isopropanol, and other topical alcohols. In addition, a number of other relatively low boiling point polyhydric alcohol solvents, which will be apparent to those of ordinary skill in the art, may be suitable. The above solvents may of course be used either alone or in various mixtures and combinations, which combinations may also include such low boiling point solvents as acetone and others.

The non-aqueous solvents referred to above should be present in the compositions in the present invention in amounts from about 1 to 40 weight percent, and preferably about 14 to 20 weight percent. A particularly satisfactory product is obtained using ethanol in amounts from about 14 to 20 weight percent. In addition to the use of a non-aqueous solvent, it is essential for the properties of the compositions of the present invention that the overall composition be substantially anhydrous. As used in the instant application, the term "substantially anhydrous" means that there is preferably no water added in the stick compositions aside from that which may be present as free or combined water in the astringent aluminum compounds or as minor impurities in other components of the formulations.

In addition to the above essential components of the compositions of the present invention, a number of optional ingredients may be added which enhance the cosmetic elegance of the overall antiperspirant stick formulations. One particularly desirable additive is an emollient selected from the class comprising propoxylated alcohols. One such particularly suitable propoxylated alcohol is commercially available under the trademark Emcol 249-3K from Witco Chemical Company. Such propoxylated alcohol emollients may be present in amounts up to about 20 weight percent of the total composition, and preferably about 8 to 15 weight percent.

Other emollients, either in addition to or in place of the propoxylated alcohol emollients mentioned above, may be incorporated into the compositions of the present invention in amounts up to about 4 weight percent and preferably about 2 weight percent. Examples of suitable emollients include but are not limited to isopropyl myristate (IPM), isopropyl palmitate (IPP), N-butyl phthalate, hexadecyl alcohol, polyethylene glycol (PEG-400), and various proprietary synthetic oils such as Neobee A-20 (Drew Chemical Corp.) Di-pelargonate (Emery Industries), Fluid AP (Union Carbide Corporation), and Procetyle AWS (Croda, Inc.). A particularly suitable combination of emollients includes about 8 to 15 weight percent of Emcol 249-3K and about 2 weight percent of isopropyl myristate.

Finally, a whitening agent or other pigment, such as titanium dioxide may be added to the compositions of the present invention in order to mask any mottled or unsightly appearance of the stick composition. Titanium dioxide or other pigment may be added up to an amount of about 0.5 weight percent of the total composition and preferably about 0.1 to 0.4 weight percent. A particularly satisfactory appearing product is produced using titanium dioxide in an amount of about 0.2 weight percent. If amounts of titanium dioxide or other pigments much above about 0.5 weight percent are used, there is a significant loss of slip-feel to the stick formulation.

The order or manner of mixing the various components of the antiperspirant stick formulation is not particularly critical. However, it will be evident that since one or more of the ingredients, as well as the final composition, are in solid or semi-solid form at normal room temperatures, it will be necessary to mix the ingredients together at elevated temperatures. It is only necessary that the temperatures be high enough that the normally solid or semisolid materials become liquid so that the ingredients may be thoroughly mixed to form a homogeneous composition. While suitable elevated temperatures will be evident to those of ordinary skill in the art, depending upon the particular ingredients selected, temperatures in the range of 50 to 90° C. will generally be sufficient, and unnecessarily high temperatures should be avoided in order not to initiate any degradation of the astringent aluminum compounds. Similarly, where relatively low boiling point ingredients such as ethanol are being added, the temperature of the mixture should be kept below the boiling point of such volatile ingredients as they are added.

After mixing the ingredients together at elevated temperatures, the mixture will form a relatively clear solution which may then be poured into molds or antiperspirant stick casings, many of which are well known in the art and may be selected as desired. The solution is then allowed to cool whereupon it solidifies into a rigid stick-form consistency which assumes a whitish opaque appearance. In general, the hardness or softness of the stick desired may be controlled by varying the amount of the alkylolamide present in the composition, since this ingredient forms the building block or base of the composition.

In general, the antiperspirant stick compositions of the present invention are superior to prior art water base stick formulations in terms of "pay-out" or application properties, slip-feel (lack of resistance or pulling upon application), antiperspirant efficacy, and stability. In one test stability of the systems was determined by a freeze-thaw cycle which comprises freezing the antiperspirant stick down to $-10°$ C. overnight, thawing the next day, and repeating this cycle four times. Prior art water-base antiperspirant stick compositions became mushy and sticky after being subjected to this freeze-thaw cycle, whereas the compositions of the present invention retained excellent consistency and application properties (see also Example XI below). An informal in-house panel of 15 or more individuals deemed the products of the present invention to be the most effective antiperspirant they had ever used (see also Example XII below).

The antiperspirant stick compositions of the present invention will now be described in further detail with reference to the following specific, non-limiting examples:

EXAMPLE I

An antiperspirant stick composition according to the present invention was made using an aluminum chlorhydroxidepropylene glycol complex according to U.S. Pat. No. 3,420,932 obtained from Reheis Chemical Company under the trademark Rehydrol, using the following formulation:

| Components | Wt. % |
| --- | --- |
| Rehydrol (aluminum chlorhydroxide -propylene glycol complex) | 20.0 |
| Emcol 70 (stearic acid monoethanolamide) | 26.0 |
| Propylene glycol | 26.0 |
| Emcol 249-3K (propoxylated alcohol emollient) | 11.3 |
| Anhydrous ethanol (SDA-39C) | 14.5 |
| Isopropyl myristate (IPM) | 2.0 |
| Titanium dioxide (TiO$_2$) | 0.2 |
| Perfume | q.s. |
| | 100.0 |

The formulation was prepared by slowly stirring the Rehydrol into the propylene glycol and then heating to about 80° C. to attain solution. The Emcol 70 was then slowly dissolved in the solution maintaining the temperature at about 80° C., and after adding the Emcol 249-3K, the cleared solution was cooled to about 76° C. At this temperature, the ethanol, isopropyl myristate and perfume were added followed by the titanium dioxide, and stirring was continued until a homogeneous suspension of the titanium dioxide was achieved. After slowing the stirring rate and allowing the mixture to cool to 70–72° C., the total mixture was poured into a stick casing which was then covered with a vinyl wrap. Air pockets in the stick were removed by pressing down slightly on the vinyl wrap, so that holes would not be formed in the stick due to entrapped air.

The resulting antiperspirant stick was highly effective and had excellent application properties, including pay-out, slip-feel and stability. (See Example XI and XII below).

EXAMPLE II

Another antiperspirant stick was made using Rehydrol as the astringent aluminum compound according to the following formulation:

| Components | Wt. % |
| --- | --- |
| Rehydrol | 20.0 |
| Emcol 70 | 26.0 |
| Propylene glycol | 26.0 |
| Emcol 249-3K | 12.3 |
| Anhydrous ethanol (SDA-39C) | 14.5 |
| IPM | 1.0 |
| TiO$_2$ | 0.2 |
| Perfume | q.s. |
|  | 100.0 |

This formulation was prepared by dissolving the Rehydrol and propylene glycol at 50° C. and then raising the temperature to 80° C. At this latter temperature the Emcol 70 and Emcol 249-3K emollient were dissolved in the solution. The solution was then cooled to 76° C. at which temperature the ethanol and isopropyl myristate were added. After cooling to 70° C. the perfume and titanium dioxide were added, and the mixture was finally poured at about 68–70° C.

The resulting antiperspirant stick was comparable in all respects to that of Example I.

EXAMPLE III

An antiperspirant stick was prepared using a 5/6th basic aluminum bromide (BAB), made according to U.S. patent application Ser. No. 88,206, referred to previously. The BAB was used in the following formulation:

| Components | Wt. % |
| --- | --- |
| 5/6 Basic aluminum bromide (BAB) | 20.0 |
| Emcol 70 | 26.0 |
| Propylene glycol | 26.0 |
| Emcol 249-3K | 12.3 |
| SDA-39C | 14.5 |
| IPM | 1.0 |
| TiO$_2$ | 0.2 |
| Perfume | q.s. |
|  | 100.0 |

The BAB was first dissolved in the ethanol, and in a separate vessel the propylene glycol was heated to 80° C. The Emcol 70 was added to the heated propylene glycol and heated to 80 to 85° C. until the Emcol 70 dissolved. After cooling this solution to 76° C. the BAB-ethanol solution was added, followed by the addition of Emcol 249-3K emollient, isopropyl myristate and perfume. The total mixture was then cooled to 66–68° C. and poured into stick molds.

The resulting antiperspirant stick was highly effective and had good application properties comparable to those of Examples I and II.

EXAMPLE IV

An antiperspirant stick was made using alcohol soluble basic aluminum chloride (ASC) made according to U.S. patent application Ser. No. 84,093, referred to previously. The formulation contained the following components:

| Components | Wt. % |
| --- | --- |
| Alcohol soluble basic aluminum chloride (A.S.C.) | 15.0 |
| Emcol 70 | 26.0 |
| Propylene glycol | 22.8 |
| Anhydrous ethanol SDA-39C | 35.0 |
| IPM | 1.0 |
| TiO$_2$ | 0.2 |
| Perfume | q.s. |
|  | 100.0 |

The ASC was first dissolved in the ethanol, and in a separate vessel propylene glycol was heated to 80° C. Emcol 70 was then dissolved in the hot propylene glycol and the resulting solution was cooled to 76° C. After adding the ethanol solution of ASC, the total solution was cooled to 72° C. and the isopropyl myristate, titanium dioxide and perfume were added. Finally, the total mixture was cooled to 62–64° C. and poured into molds.

The resulting antiperspirant stick was highly effective and had good application properties similar to those of previous examples.

EXAMPLE V

Another antiperspirant stick formulation based upon Rehydrol as the astringent aluminum compound has the following ingredients:

| Components | Wt. % |
| --- | --- |
| Rehydrol | 20 |
| Emcol 70 | 30 |
| Propylene glycol | 35 |
| Anhydrous ethanol (SDA-39C) | 15 |
|  | 100 |

This formulation is prepared in the same manner as Example I. Due to the absence of emollient, this stick formulation will not be as soothing in skin feel, and the lack of a pigment will leave the stick with a slight yellow appearance.

EXAMPLE VI

An antiperspirant stick formulation is prepared based upon Rehydrol according to the following formulation:

| Components | Wt. % |
| --- | --- |
| Rehydrol | 20 |
| Emcol 70 | 28 |
| Propylene glycol | 26 |
| Emcol 249-3K | 9.5 |
| Anhydrous ethanol (SDA-39C) | 14.5 |
| IPM | 2 |
|  | 100.0 |

This formulation is prepared in the same manner as in Example I and Example V. As in Example V, the omission of a pigment such as titanium dioxide leaves the stick with a slight yellow appearance. However, such appearance does not detract from the effectiveness or application properties of the stick formulation.

EXAMPLE VII

An antiperspirant stick formulation is prepared based upon Rehydrol with the following ingredients:

| Components | Wt. % |
|---|---|
| Rehydrol | 20.0 |
| Emcol 70 | 27.8 |
| Propylene glycol | 26.0 |
| Emcol 249-3K | 20.0 |
| Anhydrous ethanol (SDA-39C) | 5.0 |
| IPM | 1.0 |
| TiO$_2$ | 0.2 |
| Perfume | q.s. |
| | 100.0 |

This formulation is prepared in the same manner as in Example I, and results in an antiperspirant stick with properties comparable to those of Example I, except for perhaps slightly slower drying characteristics.

EXAMPLE VIII

An antiperspirant stick formulation was prepared based upon Rehydrol, but adding aluminum chloride hexahydrate to improve antiperspirant effectiveness. The formulation was prepared with the following ingredients:

| Components | Wt. % |
|---|---|
| Rehydrol | 16.0 |
| Aluminum chloride hexahydrate (AlCl$_3$ . 6H$_2$O) | 4.0 |
| Urea (buffer) | 5.0 |
| Emcol 70 | 26.0 |
| Propylene glycol | 26.0 |
| Emcol 249-3K | 6.3 |
| Anhydrous ethanol (SDA-39C) | 14.5 |
| IPM | 2.0 |
| TiO$_2$ | 0.2 |
| Perfume | q.s. |
| | 100.0 |

The propylene glycol was heated to 80° C. and the urea was added until dissolved. While retaining the temperature at 80° C., the Rehydrol, aluminum chloride hexahydrate, Emcol 70, and Emcol 249-3K and isopropyl myristate emollients were successively dissolved in the propylene glycol solution. The resulting solution was then cooled to 76° C. and the alcohol, perfume and titanium dioxide were added. After cooling to about 68-70° C., the total mixture was poured into stick casings.

The resultant antiperspirant stick is highly efficacious and has good application and esthetic properties comparable to those of Example I.

EXAMPLE IX

An antiperspirant stick formulation is prepared based upon Rehydrol with the following ingredients:

| Components | Wt. % |
|---|---|
| Rehydrol | 20.0 |
| Emcol 70 | 27.5 |
| Propylene Glycol | 27.8 |
| Emcol 249-3K | 21.0 |
| Anhydrous ethanol (SDA-39C) | 2.5 |
| IPM | 1.0 |
| TiO$_2$ | 0.2 |
| Perfume | q.s. |
| | 100.0 |

This formulation is prepared in the same manner as in Example I, and results in an antiperspirant stick having properties comparable to those of Example VII.

EXAMPLE X

An antiperspirant stick formulation was prepared based upon the active antiperspirant systems described in U.S. Pat. No. 2,814,584. This stick formulation had the following components:

| Components | Wt. % |
|---|---|
| Aluminum Chlorhydroxide Complex | 4.2 |
| Zirconyl Chloride Octahydrate | 4.5 |
| Urea | 11.3 |
| Emcol 70 | 26.0 |
| Propylene Glycol | 26.0 |
| Emcol 249-3K | 11.4 |
| Anhydrous ethanol (SDA-39C) | 14.4 |
| IPM | 2.0 |
| TiO$_2$ | 0.2 |
| Perfume | q.s. |
| | 100.0 |

The stick formulation was prepared by adding the aluminum chlorhydroxide complex, the zirconyl chloride octahydrate and urea to the propylene glycol to form a suspension. This suspension was then stirred and heated to 80° C. to attain solution. The Emcol 70 and remaining ingredients were then added in the same manner as in Example I, and the stick was formed in the same manner.

EXAMPLE XI

In addition to the freeze-thaw cycles referred to previously, three different shelf life studies were performed to determine the stability of the antiperspirant stick formulations of the present invention. The shelf life studies were carried out by maintaining separate antiperspirant stick samples, each for a seven month period, under three different atmospheric conditions as follows: (a) room temperature and ambient humidity, (b) 105° F. and ambient humidity, and (c) room temperature and a constant relative humidity of 75 percent. At each set of conditions specified above, antiperspirant sticks prepared according to Example I were compared with comparably aged commercial antiperspirant sticks.

After the seven month aging period, antiperspirant sticks of the present invention showed only a slight degree of instability under each of the atmospheric conditions above. This instability was manifested by a slight mottling in the form of white matter noted around the spiral (for raising the stick in the stick casing) at the center of the antiperspirant stick. However, this degree of mottling was less than that found in the comparably aged commercial antiperspirant sticks, and would hardly be noticeable to the untrained eye during normal usage.

In any event, the cosmetic feel and enhanced esthetics of the stick formulations of the present invention were not adversely affected upon aging under any of the three test conditions. In contrast, the comparably aged commercial sticks yielded a brittle, dry, dragging feel upon application to the skin. Moreover, sweating at the stick walls, which is a common problem in hydroalcoholic systems of this type, was not encountered during aging of the antiperspirant sticks of the present invention.

EXAMPLE XII

In addition to the informal in-house test of antiperspirant efficacy referred to previously, efficacy tests were also performed by an independent concern. In these independent efficacy tests, antiperspirant sticks made according to Example I were compared to a 20 percent Chlorhydrol (aluminum chlorhydroxide complex made by Reheis Chemical Company, Division of Armour Pharmaceutical Company) as a control. The 20 percent Chlorhydrol solution is generally considered a standard control in antiperspirant efficacy testing, due to its excellent activity.

The results of these independent tests were as follows:

| Test Sample | Sweat Reduction 22 hrs. after application | Confidence Limits |
| --- | --- | --- |
| 20% Chlorhydrol Solution | 34.0% | ± 7.6% |
| Rehydrol Stick (Example I) | 40.9% | ± 6.2% |

The above results indicate that the antiperspirant stick formulations of the present invention are at least as good as, and perhaps significantly better than, the standard control antiperspirant in terms of antiperspirant efficacy. More importantly, the antiperspirant stick formulations of the present invention are considerably better in terms of efficacy than the old and well known soap type antiperspirant sticks, which reduce sweating by only about 11 percent.

The present invention may be embodied in other specific forms without departing from the spirit or essential attributes thereof and, accordingly, reference should be made to the appended claims, rather than to the foregoing specification as indicating the scope of the invention.

We claim:

1. A stable astringent composition in stick form comprising a substantially anhydrous, homogeneous mixture of about 5 to 20 weight percent of an alcohol soluble astringent basic aluminum compound, about 20 to 35 weight percent of an alkylene polyhydric alcohol, about 20 to 30 weight percent of a normally solid higher fatty acid amide of an alkylolamine in which the fatty acid radical contains at least 12 carbon atoms and the alkylol groups of said alkylolamine contain from 2 to 3 carbon atoms, and about 1 to 40 weight percent of a non-toxic dermatologically acceptable non-aqueous solvent for said astringent basic aluminum compound, said weight percents being based on the total weight of the mixture, and said mixture being in stick form suitable for application to the human axilla.

2. The composition of claim 1 wherein said mixture includes up to about 20 weight percent of an emollient.

3. The composition of claim 2 wherein said emollient includes a propoxylated alcohol.

4. The composition of claim 2 wherein said emollient includes one or both of isopropyl myristate and isopropyl palmitate up to an amount of about 4 weight percent of the mixture.

5. The composition of claim 1 wherein said mixture includes up to about 0.5 weight percent of titanium dioxide.

6. The composition of claim 1 wherein said mixture includes up to about 2 weight percent of aluminum chloride hexahydrate and sufficient buffer to yield a mixture pH of at least about 3.

7. The composition of claim 6 wherein said buffer comprises a solution of urea in propylene glycol.

8. The composition of claim 1 wherein said alcohol soluble astringent basic aluminum compound is selected from the group consisting of basic aluminum bromides, basic aluminum chlorides, polyhydroxy complexes of basic aluminum chlorides, polyhydroxy derivatives of zinc and zirconium complexes of basic aluminum halides, zinc and zirconium derivatives of basic aluminum bromides and chlorides, phenolsulfonate complexes of basic aluminum chlorides, and mixtures thereof.

9. The composition of claim 1 wherein said non-toxic dermatologically acceptable non-aqueous solvent is selected from the group consisting of ethanol, isopropanol, dihydric alcohols, polyhydric alcohols, and mixtures thereof.

10. The composition of claim 1 wherein said fatty acid amide is selected from the group consisting of myristic acid, palmitic acid, and stearic acid amides of monoethanolamine.

11. A stable astringent composition in stick form comprising a substantially anhydrous, homogeneous mixture of about 15 to 10 weight percent of an alcohol soluble astringent basic aluminum compound, about 20 to 30 weight percent of propylene glycol, about 20 to 30 weight percent of stearic acid monoethanolamide, and about 14 to 35 weight percent of anyhydrous ethanol, said weight percents being based on the total weight of the mixture, and said mixture being in stick form suitable for application to the human axilla.

12. The composition of claim 11 wherein said astringent basic aluminum compound is selected from the group consisting of alcohol soluble basic aluminum chlorides, alcohol soluble basic aluminum bromides, alcohol soluble polyhydroxy complexes of basic aluminum chlorides, and mixtures thereof.

13. The composition of claim 12 wherein said mixture includes about 8 to 15 weight percent of propoxylated alcohol emollient.

14. The composition of claim 12 wherein said mixture includes about 1 to 2 weight percent of an emollient selected from the group consisting of isopropyl myristate, isopropyl palmitate, and mixtures thereof.

15. The composition of claim 1 wherein said alcohol soluble astringent basic aluminum compound includes a mixture of a basic aluminum compound, an astringent zirconium salt and a buffer to reduce acidity.

* * * * *